United States Patent [19]

Dowben et al.

[11] 4,231,750
[45] Nov. 4, 1980

[54] METHODS FOR PERFORMING CHEMICAL ASSAYS USING FLUORESCENCE AND PHOTON COUNTING

[75] Inventors: Robert M. Dowben, Dallas, Tex.; James R. Bunting, Boston, Mass.

[73] Assignee: Diagnostic Reagents, Inc., Dallas, Tex.

[21] Appl. No.: 860,168

[22] Filed: Dec. 13, 1977

Related U.S. Application Data

[63] Continuation-in-part of Ser. No. 634,797, Nov. 24, 1975, abandoned.

[51] Int. Cl.² ............... G01N 33/16; G01N 31/14; G01N 21/22
[52] U.S. Cl. ............... 23/230 B; 23/915; 424/8; 424/12; 435/4; 250/459
[58] Field of Search ............ 23/230 B; 424/8, 12; 195/103.5 A; 435/4; 250/459

[56] References Cited

U.S. PATENT DOCUMENTS

| | | | |
|---|---|---|---|
| 3,453,288 | 7/1969 | McConnell | 260/326.8 |
| 3,586,859 | 6/1971 | Katz | 250/83.3 UV |
| 3,641,235 | 2/1972 | Rozman | 424/8 |
| 3,654,090 | 4/1972 | Schuurs | 195/103.5 A |
| 3,741,876 | 6/1973 | Guilbault | 195/103.5 R |
| 3,789,116 | 1/1974 | Kay | 424/12 |
| 3,826,613 | 7/1974 | Parikh | 23/230 B |
| 3,852,157 | 12/1974 | Rubenstein | 195/103.5 R X |
| 3,853,987 | 12/1974 | Dreyer | 424/1 |
| 3,854,050 | 12/1974 | Peterson | 250/429 |
| 3,875,011 | 4/1975 | Rubenstein | 195/103.5 R X |
| 3,879,262 | 4/1975 | Schuurs | 195/103.5 A X |
| 3,901,654 | 8/1975 | Gross | 23/230 B |
| 3,915,641 | 10/1975 | Goering | 23/230 R |
| 3,925,162 | 12/1975 | Kanno | 195/103.5 R |
| 3,940,475 | 2/1976 | Gross | 424/8 X |
| 3,998,943 | 12/1976 | Ullman | 424/12 |
| 4,014,745 | 3/1977 | Fletcher | 195/103.5 R |
| 4,016,043 | 4/1977 | Schuurs | 195/103.5 A |
| 4,020,151 | 4/1977 | Bolz | 23/230 B X |
| 4,062,935 | 12/1977 | Masson | 23/230 B X |
| 4,104,029 | 8/1978 | Maier | 23/230 B |
| 4,133,639 | 1/1979 | Harte | 23/230 B |

OTHER PUBLICATIONS

M. L. Franklin et al., Anal. Chem., 41(1), 2–10 (1969).
K. C. Ash et al., Anal. Chem., 43(1), 26–34 (1971).
J. D. Ingle et al., Anal. Chem., 44(4), 785–794 (1972).
H. V. Malmstadt et al., Anal. Chem., 44(8), 63A, 64A, 66A, 68A, 71A, 72A, 74A, 76A (1972).
J. A. R. Mead et al., Biochem Jour., 61(4), 569–574 (Dec. 1955).
R. H. Schneider et al., Rev. Sci. Instruments, 39(9), 1369–1371, Sep. 1968.
"Emit, The Non-Radioactive Immunoassay," Booklet by Syva Corp.

*Primary Examiner*—Sidney Marantz
*Attorney, Agent, or Firm*—Richards, Harris & Medlock

[57] ABSTRACT

Improved methods for determining very low concentrations of substances present in fluid samples are provided by employing light emitting tracer compounds and (1) counting the photons emitted therefrom while discriminating against noise, nonspecific light, and quenching effects of the sample, or (2) counting the photons emitted therefrom over a predetermined integrated light flux, or a combination of (1) and (2). Further, novel fluorescently labeled low molecular weight antigens are provided which can be employed in competitive binding techniques in which the above described photon counting methods are useful. A homogeneous competitive binding assay, employing photon emitting tracer materials, which eliminates the need for separating bound from unbound materials is also provided. Finally, a modified enzyme amplification technique is set forth employing enzymes active in the bound phase to provide assay techniques useful for extremely low concentration assays.

22 Claims, No Drawings

METHODS FOR PERFORMING CHEMICAL ASSAYS USING FLUORESCENCE AND PHOTON COUNTING

This application is a continuation-in-part of an earlier filed application, Ser. No. 634,797, filed Nov. 24, 1975, now abandoned.

BACKGROUND OF THE INVENTION

In one aspect the present invention relates to methods for performing chemical assays using photon counting. More particularly, the invention relates to the quantitative clinical chemistry determinations of very low concentrations of substances in biological media by measurement of fluorescence. In addition to fluorescence, other light emitting processes may be used, such as phosphorescence, luminescence induced by x-rays or radionuclide decay, or chemical luminescence. In another aspsect this invention relates to fluorescently labeled compounds and their use in competitive binding techniques.

Fluorescence is the physical process whereby many substances absorb light of a given wave length which excites one or more atomic electrons in the material to a higher energy level. This excitation is followed after several nanoseconds by the return of the electrons to their normal energy level, accompanied by the emission of light of a higher wave length. The wave lengths of exciting light and of emitted light in the process of fluorescence are characteristic of each substance under consideration. Fluorescence can be produced by other kinds of electromagnetic radiation such as X-rays and radionuclide decay. Phosphorescence is a related process in which the excited electron reverses spin. The process of electron energy decay in phosphorescence is slow, and light is emitted over a period as long as seconds or minutes after excitation. Luminescence is another related process in which a chemical reaction causes excitation of an atomic electron followed by light emission.

Heretofore, fluorimeters used in quantifying all of these processes have measured the flux or rate of emitted light; that is, the continuous intensity of light emitted by the substance to be analyzed. The fluorimeters heretofore used in fluorescent analyses frequently made use of filters or monochromators to limit the bands of exciting and/or emitted light to those absorbed or emitted by the substance. The methods of measuring fluorescence by these flux-type fluorimeters are well known to the art and are described in many publications, for example, F. R. Elevitch, Fluorometric Techniques In Clinical Chemistry, Boston: Little, Brown & Co. (1973).

A second type of instrumentation which can be employed to quantify the light emitted by fluorescent compounds is a photon counter. Until recently photon counters were not employed in clinical assay techniques both because of their expense and because simple photon counting, without modification for use in connection with clinical sample materials, will not provide significantly improved results over those obtainable with a fluorimeter. Thus, for clinical determinations of the amount of a substance present in low concentrations in samples of biological fluid, fluorimeters taking the above described flux-type measurements have been employed exclusively.

A type of assay which is very extensively used in clinical chemistry determinations is the radio-immunoassay. This assay is used primarily for the quantification of hormones, drugs, metabolites, organic pollutants, and other biological or biochemical substances which are present in samples in very low concentrations. The radio-immunoassay is particularly suited to chemical determinations where great sensitivity and specificity are required.

The radio-immunoassay is a member of the class of chemical determinations referred to as competitive binding assays. Competitive binding assays are typified by the immune reactions between antigens and antibodies, and may be represented for example by the following formulas:

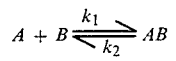

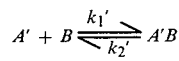

wherein A is the antigen in the unknown serum to be measured, A' is the same antigen labeled with a radioactive entity, B is a known antibody which is specific to the antigen (both to A and A'), and each k represents a reaction rate, and the ratio between $k_1$ and $k_1'$ and between $k_2$ and $k_2'$ can be determined.

Hence, when A, A' and B are placed together in a reaction medium, the antigens A and A' will compete for the binding sites on the antibody B so that some of the antigen-antibody complex will be unlabeled (AB) and some of the antigen antibody complex will be labeled (A'B). If the concentrations of A' and B are known, it then becomes a simple matter to determine the concentration of A, once the antigen-antibody complexes are separated from the reaction mixture. Thus, the radioactivity, and therefore the concentration of A', can be measured in either the fraction containing the antigen-antibody complexes or the fraction containing the remaining unreacted reaction mixture. The concentration of A is then inversely related to the radioactivity in the complexes and directly related to the radioactivity remaining in the unreacted reaction mixture. Any combination of ligand and specific binding protein can substitute for the antigen and its specific antibody.

Essentially, a simple radio-immunoassay is performed in the following manner. First, an aliquot of solution containing an unknown quantity of antigen or ligand is incubated with a known quantity of specific antibody or specific binding protein plus a known quantity of antigen or ligand labeled with a radioactive atom. The unlabeled, unknown antigen or ligand and the radioactivity labeled antigen or ligand compete with each other for binding sites on the antibody. After incubation, the antigen-antibody complexes (partly unlabeled and partly labeled) are separated from unbound antigen by any of a number of well known techniques, such as covalently bonding the antibody to or adsorbing the antibody on any of various substrates, such as activated charcoal, glass, plastic beads, test tube walls, etc. The radioactivity of either the bound or unbound fraction is determined, and the amount of unlabeled antigen may then be calculated or determined from a standard curve made up by doing sample runs using known amounts of unlabeled antigen. The performance of simple radio-immunoassays is described by J. Murphy, J. Clin. Endocrinol, 27, 973 (1967); ibid., 28, 343 (1968); and W. D.

Odell and W. H. Daughaday, *Principles of Competitive Binding Assays,* Philadelphia: Lippincott Co., 1971.

Radio-immunoassay has a number of disadvantages. First of all, it requires the use of radioactive materials which pose potential health hazards and require special precautions for handling, as well as the observance of various licensing requirements. Secondly, the shelf life of radioactive reagents is very limited (usually about 30 days), due in part to the decay of radioactivity, and in part to the radio-decomposition of materials which are packaged with the radioactive label or tracer. Thirdly, standard curves for a given set of reagents change rapidly with time and must be redetermined frequently. Fourthly, the separation of bound from free antigen or ligand often is tedious and difficult. Fifthly, the measurement of radioactivity is complex, time-consuming, and does not lend itself to automation. Lastly, in spite of its great sensitivity, simple radio-immunoassays may not be sufficiently sensitive for the assay of many antigens or ligands present in truly small amounts.

In order to overcome some of these disadvantages, assays have been developed in which the known antigen or ligand is labeled with an enzyme instead of with a radioactive atom. After separation of bound and free ligand, the amount of known ligand or antigen in the free phase is quantified by measurement of enzyme activity, usually by a colorimetric reaction. Such so-called enzyme-immunoassays are described by L. E. M. Miles and C. N. Hales, Nature 219, 186 (1968); E. Engvall, and P. Perlman, Immunochemistry 8, 871 (1971); A. H. W. M. Schuurs and B. K. van Weemen, U.S. Pat. No. 3,654,090; and A. H. W. M. Schurrs and B. K. van Weemen, U.S. Pat. No. 3,838,153. Because one molecule of enzyme catalyzes the conversion of many molecules of substrate to product, such enzyme-immunoassays frequently provide "amplification", and therefore higher sensitivity than comparable radio-immunoassays.

To date, in all examples of enzyme immunoassays described in the scientific or patent literature, the activity of enzyme attached to antigen or ligand is inhibited when combined with antibody or binding protein. The inhibition of enzyme activity in the bound phase prevents quantification of antigen or ligand in the bound phase, a serious shortcoming that has made it difficult to develop workable assay systems using fluorescent markers. However, the inhibition of enzyme activity in the bound phase has the advantage that it lowers the enzyme activity in the whole assay mixture. This has been utilized to develop homogeneous enzyme-immunoassays in which there is no need to separate bound from free phases because of the inhibition of the bound phase. Such homogeneous assays are described by K. E. Rubenstein and E. F. Ullman, U.S. Pat Nos. 3,817,837, 3,852,157, and 3,975,237.

While the development of enzyme-immunoassays and homogeneous enzyme-immunoassays have overcome some of the shortcomings of radio-immunoassays listed above, some disadvantages remain. It would be highly desirable, therefore, to have fluorescent assays, particularly fluorescent immunoassays, which could provide sensitivity the same or greater than radioactive assays and radio-immunoassays, so that the disadvantages of using radioactive materials could be avoided. Such fluorescent immunoassays would be even more desirable if they were simple to perform, accurate, and lent themselves to automation. Similarly, it would be advantageous to have other highly sensitive assays using light emitting substances in place of radio-active tracers. The use of fluorogenic substrates, i.e., nonfluorescent compounds that enzymes convert to fluorescent products, is well known to those schooled in the art as a means of assaying enzyme activity and many such fluorogenic substrates are commercially marketed. However, their application to the assay of enzyme activity in biological samples or in immunoassays has been generally limited by unpredictable fluorescence or quenching in the sample which interferes with fluorescence quantification.

BRIEF SUMMARY OF THE INVENTION

The above and other disadvantages of the prior art are overcome or alleviated by the methods of the present invention in which quantitative chemical assays are performed by detecting and measuring the light emitted from a tracer using photon counting techniques specially adapted for that purpose. The light emitting tracers may be fluorescent compounds, phosphorescent compounds or luminescent compounds, but fluorescent compounds are preferred. Light emissions from a sample containing the tracer are compared to a similar reference sample which does not contain the tracer, and the difference in photon emissions between the tracer sample and the reference sample is counted using a photon counting fluorimeter. One of two specially adapted photon counting techniques, or a combination thereof, is employed. The first type of modified photon counting technique basically comprises discriminating by energy level the photons emitted by the tracer materials from noise, nonspecific light, and quenching effects of the sample. The second type of modified photon counting technique provides for the measurement of photons emitted by the tracer compound over a predetermined integrated light flux. Especially effective photon counting can be effected by combining these two techniques. A photon counting fluorimeter which may be used in carrying out these modified photon counting techniques is disclosed in our copending application Ser. No. 634,796, filed Nov. 24, 1975, now abandoned, and entitled "Photon Counting Fluorimeter".

According to the methods of the present invention, the tracer or light emitting label or probe may be provided in the sample of unknown concentration in a number of different manners, depending upon the particular substance to be assayed and the concentration and nature of the sample. Thus, if the substance to be assayed is itself fluorescent, phosphorescent or luminescent, the assay may be performed directly, providing there is no significant spurious fluorescence or interference in the sample. Alternatively, if a derivative of the substance to be assayed is fluorescent or other light emitting, the substance may be simply converted to the fluorescent species and then assayed by photon counting.

The methods of the present invention are particularly advantageous for use in connection with immune reactions of antigens (or haptens) and antibodies, especially the competitive binding assays or immunoassays. Novel fluorescently labeled low molecular weight antigens are provided for use in such assays wherein the fluorescent moiety has a wavelength sufficient to avoid energy transfer from proteins present in the sample and is attached to the antigen in a manner which does not disrupt the specific binding capacity of the antigen for a specific antibody or specific binding protein.

Homogeneous competitive binding assays which eliminate the need for separating bound antigen-antibody complexes from unbound antigens (both labeled and unlabeled) are also provided using one of two techniques. In the first type of homogeneous competitive binding assay, fluorogenically labeled antigens which fluoresce only in a bound state are employed. Thus, only those labeled compounds which find a binding site will emit photons which can be measured and compared against the known quantity of labeled compound which has been added to the sample. A second type of homogeneous competitive binding assay takes advantage of energy transfer from the intrinsic fluorescent groups in the binding protein to a fluorescent moiety attached to the tracer material. Thus, once the tracer material is bound to the specific binding protein, energy transfer from the protein to the labeled compound will cause only the bound portion of the tracer compound to fluoresce measurably.

Finally, in a particularly preferred embodiment of the present invention, very low concentrations may be detected by an improved enzyme amplification process. According to this feature of the invention, an enzyme is provided which retains enzyme activity in the bound phase. It has been discovered that by employing certain enzymes which retain activity in a bound state improved fluorescent assays of enzyme activity (and therefore of the unknown antigen or ligand) can be obtained, because the sample fluid containing interference causing constituents can be discarded and only the bound phase counted using, for example, the improved photon counting methods of the present invention.

DETAILED DESCRIPTION OF PREFERRED EMBODIMENTS

The methods of the present invention contemplate the use of photon counting of fluorescence emission in chemical determinations and clinical chemistry assays, wherein a novel improved process of counting individual photons emitted by a fluorescent substance is used to quantify the amount of material present. The improved methods of photon counting can also be used to quantify the related processes of phosphorescence and chemical luminescence, where these methods of quantification may prove advantageous in particular analytical techniques. Accordingly, although the remainder of this disclosure will be directed particularly to fluorescence, it is to be understood that the disclosure and examples are equally applicable to phosphorescence and chemical luminescence.

The use of the improved methods of photon counting of fluorescent emissions, instead of fluorescence flux measurements, provides a number of important advantages to chemical analyses which substantially increase the sensitivity, versatility, accuracy and precision of the analyses. The contrast of photon counting as used in the methods of the present invention and the prior art fluorescence flux measurements can be compared to the difference in measuring radioactivity by counting radioactive disintegrations individually, for example by use of a scintillation counter, as contrasted to measurement of radio-activity by a flux meter or rate meter. As in the case of measuring radioactivity, fluorescence measurement by photon counting increases the sensitivity of the measurements by a factor of $10^4$ to $10^5$ over fluorescence flux measurements.

Photon counting, as used in the present invention, is inherently a measurement technique which produces digital data, and the data are handled digitally throughout the measurement process. It is different from the summation of individual photon events in a photomultiplier tube to produce a current or flux-dependent parameter. Ordinarily, photon counting does not involve digital to analog, nor analog to digital conversion. Further, the methods of measurement of photons employed by the subject invention are significantly modified when compared to previously known methods of photon counting. Modification of conventional photon counting techniques is necessitated because of the problems inherent in obtaining accurate measurement of photon emission from substances in solution and particularly substances in solution which contain protein and other large molecular weight compounds.

One of the problems which must be overcome in order to obtain accurate photon counting where the light emitting substance is present in a solution containing other constituents is the interference caused by light emission of such constituents. As used herein, the term "noise" is defined to mean the light emission by the sample in the absence of the fluorophore to be quantified. This noise of the sample should not be confused with the use of the term "noise" to describe interference from dark pulses in the phototube and electronics art.

A second problem encountered when photon counting is applied to clinical assay techniques is that of nonspecific light. Nonspecific light, as used herein, is defined to mean photons of lesser energy than those which are to be counted, that are produced by light scattering effects of the sample.

A third problem area in the application of photon counting to clinical assay techniques is the quenching effect of the sample fluid. As used herein "quenching" is defined to mean a reduction in quantum efficiency of the fluorophore to be counted caused by unknown compounds in the sample.

Lastly, any fluctuation in the source of exciting light during photon counting greatly effects the fluorescent signal being received and counted. Therefore, measurement using a defined amount of incident light flux significantly improves performance.

In spite of the above problems, the precision of photon counting measurements is significant since it is limited only by the number of counts determined (i.e., the time over which the counting occurs), because the precision of the signal is directly dependent upon the number of counts, while interference and noise is usually a function approximating the square root of the number of counts. For example, 3000 net counts may give 5% precision, then 300,000 counts would give a 0.5% precision. Furthermore, until counting pile-up occurs, the range of counts which can be taken is only limited by the number of decimal registers on the measuring instrument, whereas flux fluorimeters are usually limited to a range of $10^3$ units (i.e., 0.1 percent). Thus, it is possible by use of photon counting to design analytical procedures where the unknown substance may be present over a concentration range of $10^5$ or $10^6$ units or more and still achieve acceptable accuracy and precision without the necessity of dilution. This feature is particularly important in the application of this invention to automated techniques for chemical determinations.

The first type of improved method of photon counting of of the present invention which partially alleviates the problems presented in applying photon counting techniques to clinical assay procedures provides for the discrimination of the photons emitted by the fluorophore of interest from noise, nonspecific light, and quenching effects of the sample. This discrimination is accomplished by providing an apparatus employing a combination of monochromators or filters and a double beam counting method wherein the interference caused from noise and nonspecific light is automatically subtracted from the signal being received from the flourophores contained in a labeled portion of the sample. Further, the quenching effects of the sample solution are overcome by providing means which register an event on the basis of peak energy level only. Specifics with regard to photon counting in this manner are contained in copending application Ser. No. 634,796. By measuring photon emission while discriminating against noise, nonspecific light and the quenching effect of the sample, highly accurate clinical assays employing light emitting tracer compounds are possible.

A second improved method of photon counting eliminates the problem discussed above with respect to error caused by variation of the incident light to which the samples containing light emitting compounds are exposed. This problem is overcome by employing a novel source intensity monitor system described in detail in copending application Ser. No. 634,796. Basically, the source intensity monitor system provides a means by which photons are counted over a predetermined integrated exciting light flux rather than over a specified time period. By establishing a predetermined integrated exciting light flux and insuring that photon measurement will occur as a function of such total light flux, variations in the exciting light source become relatively unimportant. Thus, for example, if during a given time period a voltage variation causes the exciting light source to increase the light flux being applied to the sample the time period over which photons are measured is shortened so as to automatically attain measurement over the predetermined exciting light flux. On the other hand, should the exciting light source decrease in intensity the actual time for measurement of emitted photons would be lengthened so as to attain the predetermined integrated exciting light flux.

While either of the above types of improved photon counting methods can be employed alone in order to obtain excellent results in clinical assay type applications, a combination of these two methods especially desirable. Thus, the apparatus set forth in detail in the aforementioned copending application provides for photon measurement according to both of the above discussed improved techniques.

These improved photon counting methods, and a combination thereof, can be applied to a large number of analyses that have already been developed using fluorimetric techniques as means of quantifying the substance to be measured. In such analyses, increased sensitivity, accuracy and precision, and decreased interference from other substances or impurities are obtained by using such photon counting. In addition, other analyses which are now adapted to using gravimetric means, visible or ultraviolet spectrophotometry or colorimetry, titrations of various kinds, nephelometry or light scattering, flame or absorption photometry, radioactivity, or various other means of quantifying the end point or the substance to be measured can be adapted to utilizing photon counting as the means of quantification. In these methods also, the photon counting methods of the present invention can improve these analytical procedures with respect to sensitivity, accuracy, precision, diminished interference, and ease or simplicity of performance, as well as other factors.

There are many different substances and different types of quantitative determinations which can be made using the photon counting methods of the present invention, and no attempt is made in the following disclosure to list or describe all of the possible quantitative analyses to which the methods may be applied. Instead, the remainder of the disclosure is merely intended to be exemplary or representative of some of the major classes of quantitative determinations which can be made. Similarly, while the methods and specific examples described below specifically contemplate utilization of the apparatus briefly described above and described in detail in our copending application for "Photon Counting Fluorimeter", the disclosure of which is incorporated herein by reference, it is possible that other photon counting devices could be developed or adapted for use in connection with the methods of the present invention, and the methods are not limited to a particular photon counting apparatus. However, the apparatus of our copending application is particularly preferred, for reasons which will be apparent from reading that disclosure and the present application. In addition, some of the methods described in this invention for performing fluorescent assays may permit the development of assays that do not require photon counting; therefore, photon counting is not a requirement of this invention as the only method of quantifying fluorescence. Finally, since the photon counting methods of the present invention may be adapted to many known quantitative analyses, the following disclosure omits many sample preparation steps which are conventional or known in the art or which will be obvious to those of ordinary skill in the art.

A first type of chemical assays which may be performed using photon counting is the quantitative analysis of substances which are themselves fluorescent. Such substances are already analyzed using fluorimetric techniques, but the sensitivity of such measurements can be increased by three orders of magnitude ($10^3$) or more by use of the above described types of improved photon counting. By means of the improved photon counting methods, spurious fluorescence and interference from fluorescent impurities may be screened out where the specific absorption and emission spectra of the substances are known. This factor may obviate complex separation and purification techniques and permit direct analysis of the sample by photon counting.

Examples of fluorescent substances which may be so detected and measured include the lanthanide transition elements, which are extensively used in the fluors of television and cathode ray tubes; organic compounds such as anthranilic acid, indole, naphthalene, pyridoxal, barbiturates, serotonin, NADH, NADHP, nitrosamines, tetracyclines, reserpine, gibberellic acid, homovanillic acid, coumarins, pesticides, quinidine, quinine, riboflavin, salicylic acid, tryptophan, pyrene, and anthracene; and many dyes, particularly those used to give laundry and teeth a very white appearance. It will also be evident that the improved photon counting methods described above can effect substantial improvements in the fluorimetric techniques used to analyze complex mixtures of these fluorescent materials.

A second type of substances which may be quantitatively analyzed according to the present invention are those in which chemical derivatives of the substance are fluorescent. For example, certain substances, such as the catecholamines may be oxidized from non-fluorescent species to fluorescent species which may be readily detected and measured by the modified photon counting techniques of the present invention.

A fluorescent assay for epinephrine and norepinephrine is described by U.S. Von Euler and F. Lishajko in *Acta Physiologica Scandinavica,* Volume 51, Pages 348 et seq. (1961). According to the method, the catecholamines are isolated from urine by adsorption on alumina at a pH of 8.0 to 8.5. Following elution from the alumina with dilute acetic acid, they are oxidized by potassium ferricyanide in the presence of $Zn^{+2}$ to adrenochrome and noradrenochrome. Upon the addition of 20% sodium hydroxide, these compounds rearrange to the intensely fluorescent corresponding 3, 5, 6-trihydroxyindoles. Using presently available fluorimeters, this method is very satisfactory for determination of catecholamines in urine where the values are approximately 10 ug/liter epinephrine and 100 ug/liter norepinephrine, but the method is unsatisfactory for measuring plasma levels which are less than 0.5 ug/liter. However, using the photon counting techniques set forth above, catecholamines in plasma are easily and accurately measured.

A further type of assay which is particularly suited to the photon counting methods of the present invention is the class of competitive binding assays, which are typified by the immune reaction which forms antigen-antibody complexes. These assays are essentially analogous to the radio-immunoassays described above. Although these assays are mostly used for the determination of antigens in human or animal sera, it will be evident to those familiar with tests of this type that many variations can be worked out.

Where antigens or haptens are to be assayed by competitive binding assays, antibodies are prepared by coupling a sample of the pure low molecular weight compound to be assayed (hapten) to an antigenic protein. Haptens are coupled to antigenic proteins, and antibodies are raised according to well-known methods which are described, for example in Odell and Daughaday, op. cit.; C. A. Williams and M. W. Chase, *Methods in Immunology and Immunochemistry,* New York: Academic Press, 1967; D. H. Campbell, J. S. Garvey, N. E. Cremer, D. H. Sussdorf, Methods in Immunology, 2nd ed., New York: W. A. Benjamin, Inc., 1970. A number of antibodies are raised in different animals. The antibody to be used in a particular assay is selected according to a number of criteria, including: specificity to the hapten, i.e., low reactivity with other substances, particularly closely related molecular species that are likely to interfere; high affinity for the hapten, preferably such that the association constant is greater than $10^9$; high titer so that the antiserum may be diluted $10^3$ or more; and similar reactivity with either fluorescently labeled or unlabeled hapten. In certain assays, a specific binding protein may be used in place of the antibody. A number of specific binding proteins are described by Odell and Daughaday, op. cit., pp. 108–127. Other binding proteins include the estrogen receptor from uterus for estradiol prepared as described by B. Vonderhaar and G. C. Mueller, Biochimica et Biophyscia Acta 176, 626 (1969); the cyclic adenylic acid binding protein from bovine skeletal muscle prepared as described by E. Miyamoto, J. F. Kuo, and P. Greengard, Journal of Biological Chemistry 244, 6395 (1969); and the corticosteriod binding protein from rat brain prepared as described by B. S. McEwen and L. Plapinger, Nature 226, 264 (1970). Unless otherwise indicated the term "antibody" as used herein includes the use of any specific binding protein which may be substituted therefor.

While the labeling of antibodies with fluorescent moieties such a fluorescein isothiocyanate or tetramethylrhodamine isothiocyanate is a well known procedure, the labeling of antigens or ligands with fluorescent moieties for use in a competitive binding assay for low molecular weight compounds has not been done. Of course, antigens which are proteins have been labeled with fluorescent moieties in the past by employing technology similar to that used to label antibodies. It has been discovered, however, that when labeling antigens or ligands of low molecular weight (i.e. less than about 4,000) the nature of the fluorescent moiety and the site of its attachment to the ligand is of critical importance if the labeled substance is to be successfully employed in a fluorescent competitive binding assay.

One class of ligands which are commonly assayed are steroids, including digitalis glycoside aglycones (digoxigenin, digitoxigenin), estrogens (estradiol, estrone), progestins (progesterone and various birth control drugs), androgens (testosterone, adrenal androgens), corticosteroids (cortisol, cortisone, synthetic corticosteroids), and others. In order to best maintain the structural determinants (and thus the required specificity) in the competitive binding assays, the 3 position is preferred both for coupling to protein for raising antibodies, and for coupling to a fluorescent moiety for preparing a fluorescently labeled ligand. However, coupling to other positions of the steroid nucleus sometimes can also be used. It is usually desireable to convert the hydroxyl or keto group in the 3 position to another functional group in order to couple to a suitable fluorescent moiety. For example, a free carboxyl moiety can be produced at position 3 by reacting the steroid with succinic anhydride in pyridine. An amino group can be produced at position 3 by first oxidizing a hydroxyl group to a keto group, and then converting to an amino group by reaction with sodium cyanoborohydride and ammonium acetate in the presence of a molecular sieve. A sulfhydryl group can be produced at position 3 by reaction of the steroid with thiodiacetic anhydride and subsequent decomposition of the disulfide with dithiothreitol.

For the ligands thyroxine or triiodothyronine, coupling of the fluorescent moiety can be to either the amino group or the carboxyl group. For polypeptide ligands, coupling can in addition be made to the free amino groups of lysine or free sulfhydryl groups of cysteine. For other ligands, free amino, free sulfhydryl, or free carboxyl groups that are least involved as structural determinants of the ligand are preferred for coupling to the fluorescent moiety.

In all cases it has been discovered that when labeling low molecular weight antigens with fluorescent moieties it is important to do so in a manner which least affects the structural determinants of the antigen, thereby retaining the specific binding properties thereof.

The criteria for a useful fluorescent moiety depend upon whether (a) the bound and unbound phases will be separated and the fluorescence measured in the free ligand, (b) the bound and unbound phases will be separated and the fluoresence measured in the bound phase, or (c) a homogeneous competitive binding assay is desired. If the bound and unbound phases are to be separated, the fluorescent moiety should preferably be excited by light of a wavelength greater than about 380 nm, should have a quantum yield greater than about 0.2, and the polarity of the microenvironment should not affect the excitation and emission wavelengths. Examples of compounds that react to form suitable fluorescent moieties of this type are the following sulfhydryl reactive:
5-iodoacetamidofluorescein
pyrenemaleimide
amino reactive:
fluorescein isothiocyanate
tetramethylrhodamine isothiocyanate
2-methoxy-2,4-diphenyl-3-furanone
eosin isothiocyanate (forms a phosphorescent product)
hydroxyl reactive:
anthroyl, trifluoroacetyl mixed anhydride
carboxyl reactive:
4-bromomethyl-7-methoxycoumarin Certain fluorescent moieties cannot be used to produce low molecular weight fluorescently labeled antigens because of characteristic nonspecific binding problems. Examples of moieties which are not useful include dimethylamino naphthalene sulfonyl chloride, 1-naphthalene-anilinosulfonate, and their derivatives.

In general, a fluorescent immunoassay is performed analogously to a radio-immunoassay. Thus, an aliquot of solution containing an unknown quantity of antigen or hapten is incubated with a known quantity of specific antibody plus a known quantity of antigen or hapten labeled with a fluorescent entity or fluorophore. The unlabeled, unknown antigen and the fluorescently labeled antigen compete with each other for binding sites on the antibody. After incubation, the antigen-antibody complex is separated from the unbound antigen by any of a number of well known techniques. Thus, generally the known quantity of labeled antigen should generally be about twice as much as would be needed to completely bind the antibody if there were no competition from antigen in the unknown sample.

Among the techniques which may be used to separate the complex from the remaining antigen is the binding of the antibody to a substrate prior to addition of the competing antigens. For example, the antibody may be adsorbed on, or covalently bonded to, activated charcoal, glass beads, polymer beads, etc. A particularly suitable method is the coating of the antibody on the walls of plastic test tubes made of polyethylene, polypropylene or polystyrene as described by K. J. Catt, U.S. Pat. No. 3,646,346. The competitive binding may then be carried out in the test tube with the result that the antigen-antibody complexes will be bound to the test tube walls upon the completion of the reaction, and the unbound antigen which is in solution may be simply poured out. Of course, other methods of separation may be used, and many are known to those skilled in the art.

After separation, the fluorescence may either be detected in the antigen-antibody complexes or in the solution of unbound antigen. The amount of fluorescence in either one will depend upon the extent of competition between the unknown antigen and the known labeled antigen, thereby permitting the assay of the quantity of unknown antigen. The amount of unlabeled antigen in the unknown sample is directly proportional to the amount of labeled antigen remaining unbound in solution. Hence, the amount of unlabeled antigen may be determined from a standard curve made by running samples using known amounts of unlabeled antigen. Alternatively the light emission of the sample containing tracer compounds can be compared to that of an unlabeled portion of the sample.

It is sometimes particularly advantageous to measure the fluorescence in the separated antigen-antibody complex. Thus, the separation of the complex from the solution containing free antigen reduces the presence of interfering, extraneous fluorescent materials or from materials in the sample that quench fluorescence. For purposes of analysis, the complex may be removed from a chosen substrate by dissolving in alkaline solution.

It will also be evident that antibody as well as antigens can be labeled with fluorescent labels or tracers and utilized for immunoassays which will be substantially improved when the photon counting techniques of the present invention are used as the means of fluorescence quantification. Such fluorescently labeled antibodies can be used in direct immunoassays or in competitive binding immunoassays. In the case of using labeled antibodies in competitive binding immunoassays, it is possible to bind the antigen to a solid support when it is the aim of the assays to detect an unknown quantity of antibody. For example, to assay for unknown amounts of nuclear antibodies, insulin-binding antibodies or thyroglobulin-binding antibodies in the serum of a patient, it is possible to perform the assay by competition of the unknown antibodies with fluorescently labeled antibodies of known amount with a known amount of immobilized antigen.

Homogeneous fluorescent immunoassays have been developed in which the need for separating bound and free antigen or ligand is not necessary. Fluorescence is measured on an aliquot of the whole mixture after incubating the sample containing an unknown amount of antigen, a known amount of fluorescent antigen, and a known amount of antibody in buffer. A homogeneous assay is possible when the fluorescent ligand fluoresces only when bound to protein but not when free. Such fluorescent ligands can be prepared, for example, by reacting an amino group on the ligand with 7-chloro-4-nitrobenzo-2-oxa-1,3-diazole. The ligand product thus formed with fluoresce at about 530 nm when excited at about 480 nm only when bound to antibody, but not when free. Another type of homogeneous assay takes advantage of energy transfer from the intrinsic fluorescent groups in the binding protein to a fluorescent moiety in the ligand. For example cyclic-adenylic acid (cAMP) can be converted into a fluorescent product by treatment with chloracetaldehyde as described by J. A. Secrist, J. R. Barrio, N. J. Leonard, and G. Weber, Biochemistry 11, 3499 (1972) which binds similarly to a specific cAMP binding protein. The fluorescent cAMP product emits at about 405 nm when excited at 355 nm. The tryptophan residues in the binding protein are excited at about 305 nm and fluoresce at about 355 nm. When the fluorescent CAMP product is bound to protein, excitation at 305 nm produces fluorescence at 405 nm, owing to energy transfer from excited tryptophan residues in the binding protein to the fluorescent cAMP product, while the fluorescent cAMP product free in the mixture fluoresces only slightly when excited at 305 nm.

The fluorescent immunoassays according to the present invention have a number of important advantages over the analogous radio-immunoassays. First of all, the elimination of radioactive materials means that there are no health physics problems and no special precautions or licensing required. Secondly, the shelf life of reagents is very long (i.e., on the order of one or two years), compared to the short life of radioactive agents. Thirdly, standard curves are constant and reproducable over long periods of time, and as a result a standard curve can be supplied with a kit of reagents and the user need only check a standard point from time to time. Fourthly, in addition to the specificity achieved by virtue of the antibody specificity, additional specificity is achieved in fluorescent immunoassays by selecting the wave length of the exciting light and the wave length of the emitted light to correspond to only those of the fluorescent probe on the labeled antigen. In general, the unit cost of reagents is less than for radio-immunoassays, and the laboratory equipment and procedures are simpler, less expensive and less cumbersome than for radio-immunoassays. Finally, fluorescent immunoassays using photon counting may increase the sensitivity by as much as 3 orders of magnitude or more over radio-immunoassays.

Another type of assay according to the methods of the present invention is the class of assays of enzyme activity or concentration. According to this type of assay, an unknown sample containing an enzyme to be assayed is incubated with a substrate which is specific to the particular enzyme. A substrate is chosen which is not fluorescent in itself, but which is fluorogenic. That is, the activity of the enzyme on the substrate will cause the substrate to release fluorescent products. By carefully controlling the time and temperature of incubation and the concentration of the substrate, the amount of enzyme in the unknown sample can be calculated from the amount of fluorescent product released from the substrate. By applying the improved photon counting techniques of this invention to these assays, a great improvement in specificity, sensitivity, accuracy, precision and freedom from interferring substances can be obtained.

Finally, a particularly preferred embodiment of the present invention uses the previously known concept of enzyme amplification to increase still further the sensitivity of the assays and to decrease interference from fluorescence of extraneous materials. Enzyme amplification is based on the principle that one enzyme molecule can catalyze the formation of many molecules of fluorescent product from a non-fluorescent, but fluorogenic substrate. The enzyme amplification method may be used with virtually any of the previously described assays, by replacing the fluorescent tracer or label with an enzyme, and eventually incubating the enzyme labeled substance with the fluorogenic substrate for a controlled time and at a controlled temperature and concentration.

In cases where enzyme amplification is used, care must be taken in the selection of the enzyme and the method of formation of the enzyme conjugate, depending upon the way in which the assay is performed. For example, in a competitive binding assay, it is possible to measure either the antigen-enzyme conjugate which is not bound to the antibody or to measure the antigen-enzyme conjugate which is bound to antibody and separated by antibody binding to solid phase. In the latter case, it is essential that the enzymatic activity is retained by the antigen-enzyme-antibody complex. Thus, it has been found that some enzymes, notably glucuronidase and glucosidase frequently form conjugates where they are still active in the antigen-enzyme-antibody complex, while other enzymes such as lysozyme and amylase become inactivated and no longer catalyze the formation of fluorescent product when the antigen-enzyme complex combines with antibody. The discovery that some enzymes retain activity in a bound state allows measurement of the bound enzyme-antigen-antibody complex as opposed to the free, or unbound, enzyme labeled antigen. As was noted earlier, the measurement of the bound complex is advantageous since quenching and other effects of the sample solution (containing the free labeled antigen) can be avoided.

The fluorogenic substrate, such as 4-methylumbelliferone glucuronide is hydrolyzed by the enzyme, such as glucuronidase, to release the fluorescent product, namely 4-methylumbelliferone. Since one molecule of the enzyme complex hydrolyzes hundreds or thousands of molecules of fluorogenic substrate, the sensitivity using this procedure is increased by a factor of $10^3$ or more, and theoretically extremely low concentrations of only several molecules of unknown can be detected. Thus, the combination of enzyme amplification and photon counting detection in a fluorescent immunoassay can yield sensitivities as high as $10^{-15}$ moles of unknown antigen ($10^{-12}$ moles of the fluorogenic product).

The fluorescent labels or tracers used in the methods of the present invention may be virtually any of those commonly used in conventional fluorometric techniques. Although 4-methylumbelliferone is particularly suitable due to its intense fluorescence, the methods are by no means limited to this particular fluorescent tracer.

The methods of the present invention will now be described in more detail with reference to the following specific, non-limiting examples. In the examples, all solutions are aqueous solutions and all percents are weight percents, unless otherwise indicated.

EXAMPLE 1

A fluorescent immunoassay is provided for the determination of thyroxine in blood plasma. Antibody of high titer, high affinity, and high specificity to thyroxin is raised in rabbits challenged with thyroxine conjugated to hemerythrin using N,N'-dicyclohexylcarbodiimide according to well known methods described, for example in Odell and Daughaday, op. cit., or Campbell, et al., op. cit. Plastic tubes are coated with antibody as described by Catt, op. cit.

A fluorescent product of thyroxine for use as labeled antigen is prepared by reacting 0.010 mole thyroxine with 0.013 mole fluorescein isothiocyanate in 250 ml 1 M sodium carbonate for 24 hours. The pH is adjusted to 7 to precipitate the unreacted thyroxine. The pH is then adjusted to pH 4 to precipitate the product. The product is further purified by preparative thin layer chromatography using benzene:chloroform:ethanol:acetic acid 30:30:5:5 as developer.

10 microliters of unknown plus 1 ml of 0.01 N HEPES buffer, pH 7.4, containing 1.2 ng fluorescein labeled thyroxine, 200 mg 8-anilino-1-napthalene sulfonic acid, 6 mg sodium salicylate and 2 mg gelatin is added to a coated tube and the mixture incubated with gentle shaking for 45 minutes. The fluid is removed and its fluorescence measured by photon counting. Alternatively, the fluid is discarded and the tube drained by inverting. The antibody coat is dissolved in 1 ml 0.1 M tribasic sodium phosphate and the fluorescence counted by photon counting. The result is taken from comparison to a standard curve of fluorescence obtained by adding known amounts of thyroxine to exhaustively dialyzed pooled human serum in the concentration range 0 to 30 micrograms per 100 ml. Fluorescence measurements are performed with excitation at 480 nm and emission at 520 nm.

EXAMPLE 2

A fluorescent immunoassay is provided for the determination of digitoxin, a cardioactive digitalis glycoside. Antibody to digitoxin is raised in rabbits using digitoxigenin-3-hemisuccinate coupled to bovine serum albumin by means of N,N'-dicyclohexylcarbodiimide. Antibody of high titer, high affinity and high specificity is selected, and an appropriate dilution is used to coat plastic tubes.

A fluorescent product of digitoxigenin is prepared by reacting 0.01 mole digitoxigenin with 0.02 mole anthracenecarbonylchloride in 300 ml dimethylformamide at 80° C. for 24 hours in the presence of a molecular sieve. The product is separated from unreacted starting materials and purified by chromatography on silica gel.

100 microliters of unknown serum plus 1 ml of 0.04 M tris buffer, pH 7.5, containing 0.5 ng 3-anthroyldigitoxigenin, 2 mg gelatin, and 0.1 mg sodium azide is added to a coated tube and incubated for 45 min. The fluid is removed and the fluorescence measured by photon counting. Alternatively, the fluid is discarded and the fluorescence measured on the bound antibody phase by dissolving it in 1 ml 0.1 M tribasic sodium phosphate. The result is taken by comparison to a standard curve of fluorescence obtained by adding known amounts of digitoxin to pooled human serum in the range 0 to 8 ng per ml. Fluorescence measurements are performed with excitation at 365 nm and emission at 440 nm.

EXAMPLE 3

A fluorescent immunoassay is provided for the measurement of digoxin, also a cardioactive digitalis glycoside, in blood serum. Antibody to digoxin is raised in rabbits challenged with the 3-amino derivative of digitoxigenin (see below) coupled to bovin serum albumin by means of toluene diisothiocyanate. Antibody of high titer, high affinity and high specificity is selected, and an appropriate dilution is used to coat plastic tubes.

3-digoxigenone is prepared by refluxing 0.01 mole digoxigenin in 300 ml toluene and 30 ml cyclohexanone with 0.02 mole aluminum propoxide for 2.5 hours, and purified as described in *Organic Reactions*, vol VI, p. 234. To 0.008 mole 3-digoxigenone in 300 ml methanol containing 0.06 mole ammonium acetate was slowly added 0.07 mole sodium cyanoborohydride at room temperature and allowed to react for 5 hours. The mixture was acidified with HCL in methanol, the 3-aminodigoxigenin extracted into ethylene chloride, and purified on a silica column. The 3-aminodigoxigenin was reacted with a slight molar excess of rhodamine B isothiocyanate adsorbed on diatomaceous earth by the method of H. Rinderknecht, Nature 193, 167 (1962).

100 Microliters of unknown serum plus 1 ml of 0.5 ng rhodamine labeled digoxin in 0.04 M tris buffer, pH 7.5, containing 2 mg gelatin and 0.1 mg sodium azide is added to a coated tube and incubated for 45 min. The fluid is removed and its fluorescence measured by photon counting. Alternatively the fluid is discarded and the tube drained; the antibody coat is dissolved by adding 1 ml 0.1 M tribasic sodium phosphate and the fluorescence measured by photon counting. The result is taken from comparison to a standard curve of fluorescence obtained by adding known amounts of digoxin to pooled human serum in the range 0 to 6 ng per ml. Fluorescence measurements are performed with excitation at 535 nm and emission at 570 nm.

EXAMPLE 4

A homogeneous fluorescent immunoassay is provided for the measurement of triiodothyronine in blood plasma. Antibody of high titer, high affinity, and high specificity to triiodothyronine conjugated to bovine serum albumin using toluene diisothiocyanate.

A fluorescent product of triiodothyronine for use as a label is prepared by reacting 0.01 mole triiodothyronine and 0.013 mole 7-chloro-4-nitrobenzo-2-oxa-1,3-diazole in 200 ml dimethylsulfoxide containing 2 ml 1 M sodium hydroxide at 70° C. for 90 minutes. The product was purified by thin layer chromatography.

50 microliters of unknown serum is mixed with 1 ml of 0.01 N tris buffer, pH 8.6, containing 50 pg of the fluorescent triiodothyronine product, 2 mg gelatin and 0.1 mg sodium azide. 50 microliters of a suitable dilution of antibody in phosphate buffered saline is added and the mixture incubated for 90 minutes. The fluorescence is determined using 480 nm excitation and measuring emission at 545 nm. The result is taken from comparison to a standard curve of fluorescence obtained by adding known amounts of triiodothyronine to exhaustively dialyzed pooled human serum in the concentration range 0 to 8 ng per ml.

EXAMPLE 5

A homogeneous fluorescent immunoassay is provided for the quantification of cyclic adenylic acid. Cyclic adenylic acid binding protein and protein kinase inhibitor protein are isolated from beef muscle as described by Miyamoto, et al. op. cit.

A fluorescent product of cyclic adenylic acid is prepared by reacting 0.001 mole cyclic adenylic acid with 50 ml 1 M aqueous chloroacetaldehyde at 4° C. for 4 days with gentle stirring. During this time the pH of the mixture is maintained at 4.5 by the automatic addition of 0.1 M sodium hydroxide by a pH stat automatic titrator. The mixture is lyophilized, redissolved in water, and the unreacted chloroacetaldehyde with ether. The aqueous phase is lyophilized, redissolved in a minimal amount of wter, and the product precipitated with isopropanol.

The assay is performed in 1 ml 0.02 M potassium phosphate buffer, pH 6.3, at 4° C., to which is added (1) 10 microliters of 0.01 M sodium acetate buffer, pH 4.0, containing 1 pmole fluorescent adenylic acid product and a just maximally effective amount of inhibitor protein, usually 12 micrograms, (2) unknown samples containing varying amounts of cyclic adenylic acid in the range 0 to 20 pmoles, and (3) 50 microliters of an appropriate dilution of binding protein containing 10 micrograms bovine serum albumin. The quantity of binding protein is such that approximately ½ of the total fluorescent cAMP product is bound. The mixture is incubated for 1 hour at 4° C. and the fluorescence measured. The unknown amount of cyclic adenylic acid is taken from a standard curve obtained by using known amounts of cAMP. Fluorescence is measured using 305 nm for excitation and 410 nm for emission.

EXAMPLE 6

A fluorescent immunoassay is provided for the determination of morphine using the enzyme amplification method. Antibody of high titer, high affinity and high specificity to morphine is raised in rabbits using an antigen formed by coupling morphine glucuronide to bovine plasma albumin by means of a DCC condensation. Antibody is precipitated, dissolved, assayed and coated on plastic test tubes in the same manner as described in the preceding examples.

Serum containing unknown quantities of morphine is diluted 1:2000 with 0.01 M tris amine buffered saline. A morphine-glucuronidase conjugate is prepared by refluxing morphine and glucuronidase with succinic anhydride, as described by Lieberman, Erlanger, Beiser and Agate, *Recent Progress in Hormone Research*, Volume 15, pp. 165 et seq. (1959). To an antibody coated test tube containing 5 ml 0.01 M tris amine buffer are added 0.1 ml of the diluted unknown serum and 0.1 ml of a known concentration solution of the morphine-glucuronidase conjugate. A parallel test tube is prepared using the same ingredients as described above, but without the glucuronidase conjugated to the morphine. The test tubes are then incubated at 37° C. for 45 minutes, and the contents are poured out and the tube drained.

The bound morphine-enzyme assayed in the test tube for glucuronidase activity using the fluorogenic substrate 4-methylumbelliferone-D-glucopyranoside for a controlled time and at a controlled temperature. The glucuronidase is not itself fluorescent, the contents are assayed for glucuronidase activity by subjecting the contents to a fluorogenic substrate, such as 4-methylumbelliferone glucuronide as described in Mead, Smith and Williams, *Biochemical Journal*, Volume 61, pp. 569 et seq. (1955). The liberated 4-methyl-umbelliferone is measured by photon counting, and the amount of morphine present in the unknown serum is determined by comparison to standard curves obtained by running similar sera to which known amounts of morphine were added.

The present invention may be embodied in other specific forms without departing from the spirit or essential attributes thereof and, accordingly, reference should be made to the appended claims, rather than to the foregoing specification as indicating the scope of the invention.

What is claimed is:

1. In a competitive binding assay method for determining the concentration of a substance in a fluid sample which comprises providing a light emitting tracer compound and detecting the amount of tracer to determine the concentration of the substance the improvement comprising detecting said tracer by a photon counting method which (1) discriminates the photons emitted by said tracer from noise and non-specific light by subtracting the counts emitted by a tracer free sample and, (2) discriminates the photons emitted by such tracer from the quenching effects of the sample by counting only those photons of a predetermined pulse height.

2. The method of claim 1 and further comprising counting the photons emitted by said tracer compound over a predetermined integrated light flux.

3. The method of claim 1 wherein said light emitting tracer compound is selected from the group consisting of fluorescent compounds, phosphorescent compounds and luminescent compounds.

4. The method of claim 1 wherein said light emitting tracer is a fluorescent compound.

5. The method of claim 1 wherein the concentration of the substance is determined by subtracting the photons emitted from a portion of the sample not containing tracer compounds from the total amount of photons emitted from the tracer compound containing portion of the sample.

6. The method of claim 1 wherein the concentration of the substance is determined by comparing the photons emitted by the sample containing the tracer compound to photons emitted from a standard sample.

7. The method of claim 1 wherein said tracer compound is provided by a chemical reaction which converts said substance from a species which does not emit light to a derivative of said substance which does emit light.

8. The method of claim 1 wherein said substance is a species which emits light and said substance and said tracer are one and the same.

9. The method of claim 1 wherein said substance is an antigen or antibody and said method comprises the steps of binding said substance to its corresponding antigen or antibody and attaching said tracer compound to the resulting antigen-antibody complex.

10. The method of claim 1 wherein said substance and said tracer compound participate in a competitive binding reaction.

11. The method of claim 10 wherein said substance is an antigen and the method includes the steps of providing a known quantity of an antibody specific to said antigen, attaching said tracer to a known quantity of antigen, comparatively binding said substance and said tracer-containing antigen to said antibody to form antigen-antibody complexes and separating said complexes from the unbound antigen.

12. The method of claim 11 wherein said antibody is attached to a substrate prior to said competitive binding reaction.

13. The method of claim 11 wherein the light emissions from said antigen-antibody complexes are measured.

14. The method of claim 11 wherein the light emissions from the unbound tracer-containing antigen are measured.

15. The method of claim 11 wherein said antigen is of low molecular weight and said tracer comprises a fluorescent moiety which is attached to said antigen in a manner such that the structural determinants thereof are not disrupted.

16. The method of claim 15 wherein said fluorescent moiety is excited by a wavelength greater than about 380 nm and has a quantum yield greater than about 0.2.

17. The method of claim 1 wherein said substance is an enzyme and said tracer compound is provided by incubating the sample containing the enzyme with a substrate specific to said enzyme, said substrate being capable of producing a light emitting entity when acted on by said enzyme and controlling the time, temperature and concentration of the incubation of substrate and enzyme, whereby the light emission will be directly proportional to the enzyme activity and the concentration of the enzyme in the sample.

18. The method of claim 1 wherein said tracer compound is provided by the reaction product of an enzyme and a substrate specific to said enzyme, said substrate-enzyme complex determining the amount of light emitting entity generated.

19. The method of claim 18 wherein said enzyme is attached to a known quantity of an antigen or an antibody, and said substance and said known quantity of enzyme labeled antigen or antibody compete in a competitive binding reaction to form antigen-antibody complexes some of which will contain said enzyme.

20. The method of claim 19 wherein said enzyme-antigen-antibody complexes are incubated with said substrates specific to said enzymes to release said light emitting entity.

21. The method according to claim 20 wherein said enzyme is selected from the group consisting of glucuronidase and glucosidase.

22. The method of claim 19 wherein after said competitive binding reaction, the unbound enzyme labeled antigen or antibody is incubated with said substrates specific to said enzyme to release said light emitting entity.

* * * * *